United States Patent [19]

LeBlanc et al.

[11] Patent Number: 4,688,426
[45] Date of Patent: Aug. 25, 1987

[54] HYDROMETER FOR DETERMINATION OF IMMUNOGLOBULIN CONTENT OF MARE COLOSTRUM

[75] Inventors: Michelle M. LeBlanc, Newberry; James F. Parker, Gainesville; Charles F. Rabbit, Gainesville; Donald J. Wallace, Gainesville, all of Fla.

[73] Assignee: University of Florida, Gainesville, Fla.

[21] Appl. No.: 800,046

[22] Filed: Nov. 20, 1985

[51] Int. Cl.⁴ .............................................. G01N 9/12
[52] U.S. Cl. ..................................................... 73/450
[58] Field of Search .................................. 73/450, 448

[56] References Cited

U.S. PATENT DOCUMENTS

| | | | |
|---|---|---|---|
| 748,838 | 1/1904 | Broestler | 73/450 |
| 2,006,549 | 7/1935 | Hartley | 73/450 |
| 2,506,973 | 5/1950 | Segal | 73/450 |

Primary Examiner—John Chapman
Attorney, Agent, or Firm—Dennis P. Clarke

[57] ABSTRACT

A hydrometer for determination of immunoglobulin content of mare colostrum comprises a container having a top wall, side walls and an open bottom. An elongate, emergent stem is carried by and projects from the top wall, and the stem is provided with a scale along its length to indicate the specimen specific gravity when the device is immersed in water. A partition wall for the container is positioned between the top wall and the open bottom dividing the container into an upper air chamber and a lower specimen chamber. A removable closure member is used for the open bottom of the container. The closure member is sized to adjust the specimen chamber to a predetermined volume when fully inserted in the open bottom of the container. A bleed vent contained in the side wall of the closure member, allows excess specimen and air bubbles to escape.

3 Claims, 3 Drawing Figures

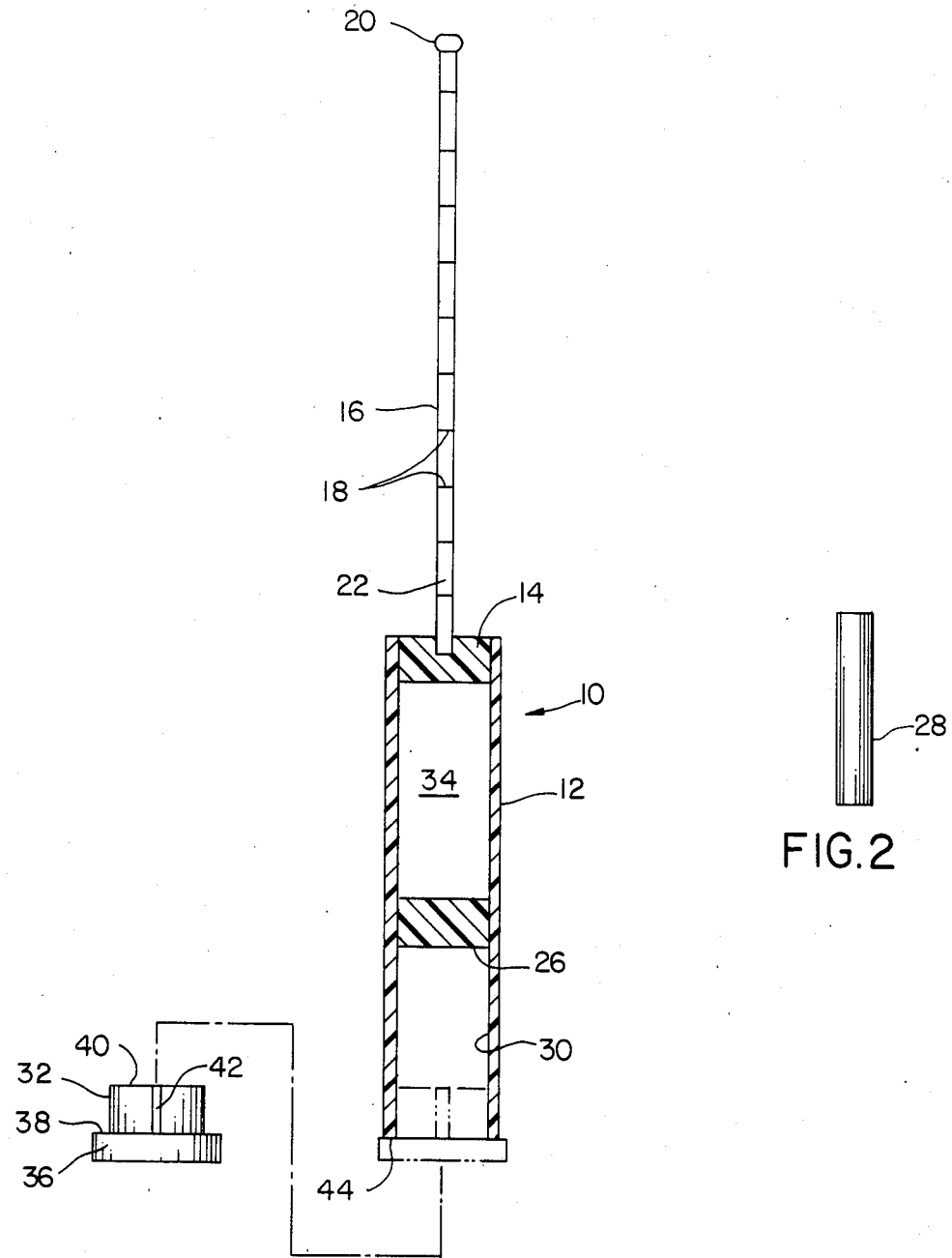

HYDROMETER FOR DETERMINATION OF IMMUNOGLOBULIN CONTENT OF MARE COLOSTRUM

THE INVENTION

This invention is an instrument which determines the specific gravity of colostrum collected from a mare following the birth of a foal. It is preferable that this determination be made prior to the foal suckling using a small amount of colostrum.

BACKGROUND OF THE INVENTION

Maternal immunoglubulins (Ig, antibodies) derived from colostrum are the single most important factor in protecting a neonatal focal from disease. Millions of dollars are spent annually on the treatment of foals which fail to attain adequate serum Ig levels. Many of these foals die even when vigorous treatment is instituted. Others never reach full potential due to debilitating infections.

Due to the mare's epitheliochorial placentation and separation of maternal and fetal circulations, transplacental transfer of material antibody does not occur. Foals must rely on adequate intake and absorption of colostral Ig for resistance to infectious diseases during the first few weeks of life. Ingestion of colostrum must occur soon after birth since the ability of the gut to absorb Ig is time dependent. An absorption rate of 100 percent at birth decreases to zero within 12 to 18 hours.

Low Ig concentration in mare colostrum has been incriminated as being the major cause of failure of passive transfer. However no commercial "on the farm" technique is available to assess Ig content in mare colostrum and estimation of Ig content by the appearance and consistency of colostrum can be misleading. Thick viscous samples may not be good indicators of quality. Test kits on the market measure serum IgG levels in foals greater than 18 hours of age, a time when no further absorption of Ig can occur.

We have found a linear relationship between colostral specific gravity and colostral Ig levels. This relationship served as the basis for the "colostrometer" which estimates Ig content of colostrum. The "colostrometer" has been field tested on Thoroughbred, Quarter Horse, Arabian and Standarbred farms and found to be a practical, rapid and accurate method for determining colostral IgG. The ability to detect low colostral Ig levels immediately postpartum will allow the farm manager or veterinarian to identify those foals at high risk for disease and supplement them with colostrum higher in IgG content.

Significant differentiation of a colostrum specimen occurs over a narrow range of specific gravity between 1.040 and 1.100. The test must be performed under field conditions thereby not allowing use of radio-immunodiffusion assays which would be used under laboratory conditions. The material is opaque, viscous, and adhesive. These factors, together with the limited sample volume, do not allow the use of conventional hydrometers or equivalent refractometer methods.

BRIEF SUMMARY OF THE INVENTION

The invention can be defined as a hydrometer for determination of immunoglobulin content of mare colostrum consisting of a container having a top wall, side walls and an open bottom. An elongate, emergent stem is carried by and projects from the top wall, and the stem is provided with a scale along its length. A partition wall for the container is positioned between the top wall and the open bottom dividing the container into an upper air chamber and a lower specimen chamber. A removable closure member is used for the open bottom of the container. The closure member is sized to adjust the specimen chamber to a predetermined volume when fully inserted in the open bottom of the container. The closure member contains a bleed vent in the side wall allowing for excessive specimen to be forced outwardly.

BRIEF DESCRIPTION OF THE DRAWING

FIG. 1 is a partially sectional view of a preferred embodiment of the present inventions;

FIG. 2 is a plan view of a spacer for use in assembling the device illustrated in FIG. 1.

DETAILED DESCRIPTION OF THE INVENTION

Figure 3:
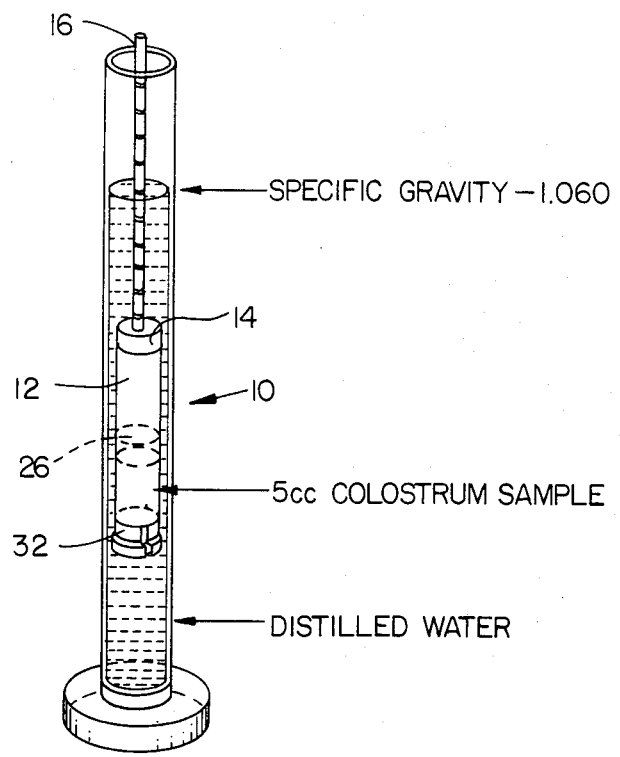
FIG. 3 is a perspective view illustrating the Hydrometer in use.

Referring to FIG. 1, 10 designates a hydrometer constructed in accordance with the design of the present invention. The hydrometer 10 comprises a container 12, which in the preferred embodiment is constructed of plastic and is cylindrical in cross-section. In an example of the invention container 12 is 85.96 millimeters in length and has a diameter of 16 millimeters.

Mounted in the upper end of the container 12 is top 14 having a thickness of about 13 millimeters. The top 14 is bored to receive a stem 16 which as indicated in the drawing is provided with a scale 18 having lines such that, when in use and floating in water the specific gravity of a specimen can be read directly from the scale at the water surface. Significant differentiation of specimens occurs over a narrow range of specific gravity between 1.040 and 1.100. The upper end of the stem 16 is closed with an epoxy resin indicated at 20.

Inside the lower end of the stem 16 there may be placed a small stainless steel wire, cut to adjust the device after final assembly such that, when it is placed in distilled water at 20° C. and with the specimen container shown at 30 filled with distilled water the first mark of 1.000 may be read. The adjustment wire is designated 22 in FIG. 1 of the drawing. Between the top 14 and the open bottom of the device is a partition member 26. In the manufacture of the hydrometer it is advisable to place the partition member 26 by means of an assembly spacer 28 illustrated in FIG. 2. The assembly spacer 28 is placed in the lower chamber or specimen chamber 30 of the hydrometer. A removable closure 32 is inserted in the open bottom which presses the assembly spacer 28 into engagement with the partition member 26. This positions the partition so that the specimen chamber of the hydrometer will hold exactly 5 milliliters. After the partition has been properly positioned the assembly spacer is removed and the partition 26 is cemented in place.

In a prototype hydrometer the partition has a thickness of 13 millimeters. A portion of the container wall and the top 14 and partition 26 define a flotation or air chamber designated 34.

The plug 32 is provided with a rim 36 and the height of the plug between the surface 38 of the rim and the surface 40 of the plug is 11.557 millimeters.

The closure member 32 is provided with a bleed vent 42 which extends from wall 40 to wall 38. The function of the bleed vent is to permit air bubbles and excess colostrum placed in the chamber 30 to be forced outwardly so that when the plug is fully seated the retained volume is, as set forth, exactly 5 milliliters.

The air balanced compartment 34 is sized to provide a total displacement force which is sufficient to overcome the weight of the device sufficiently to cause it to float in water with the stem 16 above the water surface to the 1.000 mark on scale 18 when the specimen compartment is filled with material at the lowest specific gravity. The lowest specific gravity is 1.000 or 1.000 gram per milliliter.

The stem diameter is determined by the desired rate of emergent flotation per unit of change in specimen specific gravity. In the present case a scale rate of 11 millimeters per 0.050 grams is selected corresponding to a stem diameter of 2.413 millimeters. In a prototype device the stem was made of stainless steel tubing to provide sufficient strength in the small diameter. All of the other parts of the device were made of transparent plastic materials.

In operation, the specimen is placed in the specimen container 30 and the plug or closure member 32 is inserted in the open bottom to expel excess specimen and the closure is pressed inwardly until the rim face 38 engages the lip 44 of the device. The specimen filled hydrometer is then placed in water at a temperature of about 20° C. It has been found that as the jacket water temperature is increased (for example 30° C.) the indicated specific gravity will increase to indicate an error as large as 0.010.

What is claimed is:

1. A hydrometer consisting of a container having a top wall, side walls and an open bottom, an elongate, emergent stem carried by and projecting from the top wall, said stem being provided with a scale along its length, a partition wall for the container positioned between the top wall and the open bottom dividing said container into an upper air chamber and a lower liquid specimen chamber, a removable closure member for the open bottom of the container, said closure member having a bottom and side walls and sized to adjust the specimen chamber to a predetermined volume when fully inserted in the open bottom of the container and a bleed vent formed in a part of one of said side walls of the closure member, said vent being posititioned so as to permit air bubbles and excess liquid specimen to bleed from said liquid specimen chamber when said closure member is inserted in said open bottom of said container.

2. The hydrometer as defined in claim 1 further including an adjustment wire positioned on the emergent stem.

3. The hydrometer as defined in claim 2 wherein the volume of the specimen chamber is 5 milliliters.

* * * * *